(12) United States Patent
Kim et al.

(10) Patent No.: US 9,446,953 B2
(45) Date of Patent: Sep. 20, 2016

(54) FABRICATION OF METALLIC HOLLOW NANOPARTICLES

(75) Inventors: Jae-Woo Kim, Newport News, VA (US); Sang H. Choi, Sr., Poquoson, VA (US); Peter T. Lillehei, Yorktown, VA (US); Sang-Hyon Chu, Newport News, VA (US); Yeonjoon Park, Yorktown, VA (US); Glen C. King, Williamsburg, VA (US); James R. Elliott, Yorktown, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 432 days.

(21) Appl. No.: 12/315,519

(22) Filed: Dec. 4, 2008

(65) Prior Publication Data

US 2009/0203196 A1  Aug. 13, 2009

Related U.S. Application Data

(60) Provisional application No. 61/005,329, filed on Dec. 4, 2007.

(51) Int. Cl.
| | |
|---|---|
| B22F 9/24 | (2006.01) |
| C01B 19/00 | (2006.01) |
| B01J 13/02 | (2006.01) |
| B22F 1/00 | (2006.01) |
| B82Y 5/00 | (2011.01) |

(Continued)

(52) U.S. Cl.
CPC .............. *C01B 19/007* (2013.01); *B01J 13/02* (2013.01); *B22F 1/0018* (2013.01); *B22F 9/24* (2013.01); *B82Y 5/00* (2013.01); *B82Y 30/00* (2013.01); *B22F 2001/0029* (2013.01); *H01L 21/02428* (2013.01)

(58) Field of Classification Search
None
See application file for complete search history.

(56) References Cited

U.S. PATENT DOCUMENTS

| | | |
|---|---|---|
| 4,491,679 A | 1/1985 | Moore |
| 4,686,320 A | 8/1987 | Novak et al. |

(Continued)

OTHER PUBLICATIONS

Esumi, K. et al., "Role of Poly(amidoamine) Dendrimers for Preparing Nanoparticles of Gold, Platinum, and Silver", Langmuir 2000, vol. 16, pp. 2604-2608, Published on Web Feb. 3, 2000.*

(Continued)

*Primary Examiner* — George Wyszomierski
(74) *Attorney, Agent, or Firm* — Jennifer L. Riley; Robin W. Edwards (57) ABSTRACT

Metal and semiconductor nanoshells, particularly transition metal nanoshells, are fabricated using dendrimer molecules. Metallic colloids, metallic ions or semiconductors are attached to amine groups on the dendrimer surface in stabilized solution for the surface seeding method and the surface seedless method, respectively. Subsequently, the process is repeated with additional metallic ions or semiconductor, a stabilizer, and $NaBH_4$ to increase the wall thickness of the metallic or semiconductor lining on the dendrimer surface. Metallic or semiconductor ions are automatically reduced on the metallic or semiconductor nanoparticles causing the formation of hollow metallic or semiconductor nanoparticles. The void size of the formed hollow nanoparticles depends on the dendrimer generation. The thickness of the metallic or semiconductor thin film around the dendrimer depends on the repetition times and the size of initial metallic or semiconductor seeds.

18 Claims, 5 Drawing Sheets

(51) Int. Cl.
*B82Y 30/00* (2011.01)
*H01L 21/02* (2006.01)

(56) References Cited

U.S. PATENT DOCUMENTS

| | | | |
|---|---|---|---|
| 5,487,952 A | 1/1996 | Yoo et al. | |
| 6,590,056 B2 | 7/2003 | Won et al. | |
| 6,649,138 B2 * | 11/2003 | Adams et al. | 423/403 |
| 6,664,315 B2 | 12/2003 | Tomalia et al. | |
| 6,849,361 B2 | 2/2005 | Fukuda et al. | |
| 6,866,764 B2 | 3/2005 | Dalman et al. | |
| 8,017,181 B2 * | 9/2011 | Shin et al. | 427/215 |
| 8,083,986 B2 | 12/2011 | Choi et al. | |
| 8,217,143 B2 | 7/2012 | Kim et al. | |
| 8,529,825 B2 | 9/2013 | Chu et al. | |
| 2002/0045714 A1 | 4/2002 | Tomalia et al. | |
| 2002/0068795 A1 | 6/2002 | Won et al. | |
| 2003/0032709 A1 | 2/2003 | Toshima et al. | |
| 2004/0070094 A1 | 4/2004 | Tomalia et al. | |
| 2004/0072937 A1 | 4/2004 | Tomalia et al. | |
| 2004/0166166 A1 | 8/2004 | Matsunami et al. | |
| 2007/0240749 A1 | 10/2007 | Ohtaki | |
| 2009/0004086 A1 | 1/2009 | Kuhling et al. | |
| 2009/0072078 A1 | 3/2009 | Choi et al. | |
| 2009/0099044 A1 * | 4/2009 | Hutchison et al. | 506/30 |
| 2009/0185942 A1 | 7/2009 | Choi et al. | |

OTHER PUBLICATIONS

Kalele, S., et al., "Nanoshell particles: synthesis, properties and applications", Current Science, vol. 91, No. 8, Oct. 25, 2006, pp. 1038-1052.*

Crooks, Richard M. et al., "Dendrimer-Encapsulated Metal Nanoparticles: Synthesis, Characterization, and Applications to Catalysis", Accounts of Chemical Research, vol. 34, No. 3, Mar. 2001, pp. 181-190.*

M. Zhao, at al, "Preparation of Cu Nanoclusters within Dendrimer Templates," J. Am. Chem. Soc. 1999, pp. 4877-4878, vol. 120.

L. Balogh, at al., "Poly Dendrimer-Temiplated Nanocopmposites," J. Am. Chem, Sec 1998, pp, 7355-7356, vol. 120.

M. Zhao, et al., "Homogeneous Hydrogenation Catalysis with Moriodisperse, Dendrimer-Encapsulated Pd and Pt. Nanoparticles," Angew. Chem. Int. Ed. Engl., 1999, pp. 364-366, vol. 38, No. 3.

M. E. Garcia, et al., "Preparation and Characterization of Dendrimer-Gold Colloid Nanocomposites," Anal Chem., 1999, pp. 256-258, vol. 71.

M. Zhao, et al., "Dendrimer-Encapsulated Pt Nanoparticles:Synthesis, Characterization, and Applications to Catalysis," Adv. Mater., 1999, pp. 217-220, vol. 11, No. 3.

K. Sooklal, et al., Adv. Mater., "A Blue-Emitting Cds/Dendrimer Nanocomposite", 1998, pp. 1083-1087,vol. 10, No. 14.

C. Schonenberger, et al, "Template Synthesis of Nanowires in Porous Polycarbonate Membames: Electrochemistry and Morphology", J. Phys. Chem, B, 1997. pp. 5497-5505, vol. 101.

K. B. Shelimov, et al., Chem. Mater., "Composite NanoStructures Based on Template Boron Nitride Nanotubes" 2000, pp. 250-254. vol. 12, No. 1.

D. A. Tomalia, et al., Starburst Dendrimers: Molebular-Leval Control of Size, Shape, Surface Chemistry, Topology, and Flexibility from Atoms to Macroscopic Matter, 1990, Angew, Chem. Int. Ed. Engl., pp. 138-175, vol. 29.

J. F. G. A. Jansen, et al., "Encapsulation of Guest Molecules into a Dendritic Box,"Science, Nov. 13, 1994, pp. 1226-1229, vol. 266.

H. Abe, et al., "Surface Plasmon Absorption of Various Colloidal Metal Particles," Chem. Phys., 1982, pp. 137-141, vol. B8.

S. J. Oldenburg,"Nanoengineering of Optical Resonances," Chem. Phys. Left., May 22, 1998, pp. 243-247, vol. 288.

E. Prodan, et al., "A Hybridization Model for the Plasmon Response of Complex Nanostructures," Science, Oct. 17, 2003, pp. 419-422, vol. 302.

* cited by examiner

*Figure 4. (a and b) FE-SEM and (c and d) STEM images of hollow Au nanoparticles prepared by (a and c) the seeding method and (b and d) the seedless method.*

FIG. 5

FABRICATION OF METALLIC HOLLOW NANOPARTICLES

CROSS-REFERENCE TO RELATED APPLICATION

This Application claims the benefit of U.S. Provisional Application No. 60/005,329, filed on Dec. 4, 2007 for "Fabrication of Metallic Hollow Nanoparticles." This application is related to copending U.S. application Ser. No. 11/827,567 filed on Jul. 12, 2007 for "Fabrication of Metal Nanoshells," U.S. application Ser. No. 12/313,945, filed on Nov. 26, 2008 for "Metallized Nanotube Polymer Composite (MNPC) and Methods for Making Same", U.S. application Ser. No. 11/831,233, filed on Jul. 31, 2007 for "Configuration and Power Technology for Application-Specific Scenarios of High Altitude Airships," and U.S. application Ser. No. 12/315,520, filed on Dec. 4, 2008 for "Fabrication of Advanced Thermoelectric Materials by Hierarchical Nanovoid Generation." all of which are hereby incorporated by reference herein.

STATEMENT REGARDING FEDERALLY SPONSORED RESEARCH OR DEVELOPMENT

The U.S. Government has a paid-up license in this invention and the right in limited circumstances to require the patent owner to license others on reasonable terms, as provided for by the terms of Contract No. NCC-1-02043 awarded by the National Aeronautics and Space Administration, and Science and Technology Corporation Contract Nos. L-71200D and L-71407D.

BACKGROUND OF THE INVENTION

1. Field of the Invention

This invention relates generally to nanoscale particles. It relates particularly to a process for fabricating hollow metal nanostructures, or metal nanoshells, employing amine terminal dendrimer molecules to fabricate a metal lining on a dendrimer.

2. Description of Related Art

A great interest currently exists in the synthesis and characterization of hollow metal nanostructures, because of their surface properties and catalytic activities, which are different from their solid counterparts. Most early work in this field involved hollow nanostructures of several hundreds of nanometers. Recently, the preparation of hollow nanostructures on the scale of tens of nanometers was demonstrated, employing a replacement reaction with a solid silver template and a nanoscale Kirkendall effect, respectively. However, such a fabrication process is very complicated, and requires the use of organic solvents. Moreover, it has been found generally difficult to form stable hollow metal nanoparticles, and even solid metal nanoparticles, because of strong magnetic interactions in magnetic particle systems.

BRIEF SUMMARY OF THE INVENTION

Accordingly, it is a primary object of the present invention to provide what is not available in the art, viz., an uncomplicated, yet highly efficacious process for the fabrication of hollow metal nanostructures, or metal nanoshells. Moreover, it is another primary object of the present invention to provide a process which produces hollow metal nanoparticles which are stable and for use in high performance thermoelectric (TE) materials in order to achieve a high figure of merit (ZT) in their structures, for electrically efficient nano- and micro-scale batteries, fuel cells, and other power-related devices. Metallic and semiconductor nanoshells can be fabricated via this process to specified diameters and wall thicknesses to optimize the desired characteristic behaviors most suitable for the specific application.

These primary objects and their attending benefits are achieved by providing a process for the fabrication of metal or semiconductor nanoshells, which process includes providing at least one amine terminal dendrimer molecule and promoting growth of the amine terminal dendrimer, preferably by use of ammonia or ethylene diamine, to form a dendrimer structure, having at least one surface amine group, for use as a template for the metallic or semiconductor nanoshells. The metal is preferably a transition metal, such as gold, copper, silver, palladium, nickel, iron, cobalt, manganese or platinum. In the case of a semiconductor, the semiconductor is preferably cadmium sulfide. The dendrimer molecule is preferably an amine-terminated poly (amidoamine) (PAMAM) dendrimers (G4(NH$_2$), where G4 represents the 4$^{th}$ generation) or hydroxyl-terminated PAMAM (G5(OH)). The dendrimer structure formed is preferably a three-dimensional hyperbranched polymer. At least one metallic ion or a semiconductor is attached to at least one surface amine group. This step is repeated along with adding a stabilizer, such as boric acid, thiol terminated chemical molecules or a solvent, and a reducing agent, such as NaBH$_4$, such that a wall forming the metallic or semiconductor nanoshell is formed. The dendrimer structure is then removed, preferably thermally or chemically.

Potential applications of the metal nanoshells include enhanced MRI diagnostic contrast agents, tumor hyperthermia therapies, retinal detachment therapies, and magnetic field-guided drug delivery systems and radioactive therapies.

BRIEF DESCRIPTION OF THE SEVERAL VIEWS OF THE DRAWINGS

For a more complete understanding of the present invention, including its primary objects and attending benefits, reference should be made to the DETAILED DESCRIPTION OF THE INVENTION, which is set forth below. This Detailed Description should be read together with the accompanying Drawings, wherein.

DETAILED DESCRIPTION OF THE INVENTION

The following detailed description is of the best presently contemplated mode of carrying out the invention. This description is not to be taken in a limiting sense, but is made merely for the purpose of illustrating general principles of embodiments of the invention.

Figure 1:
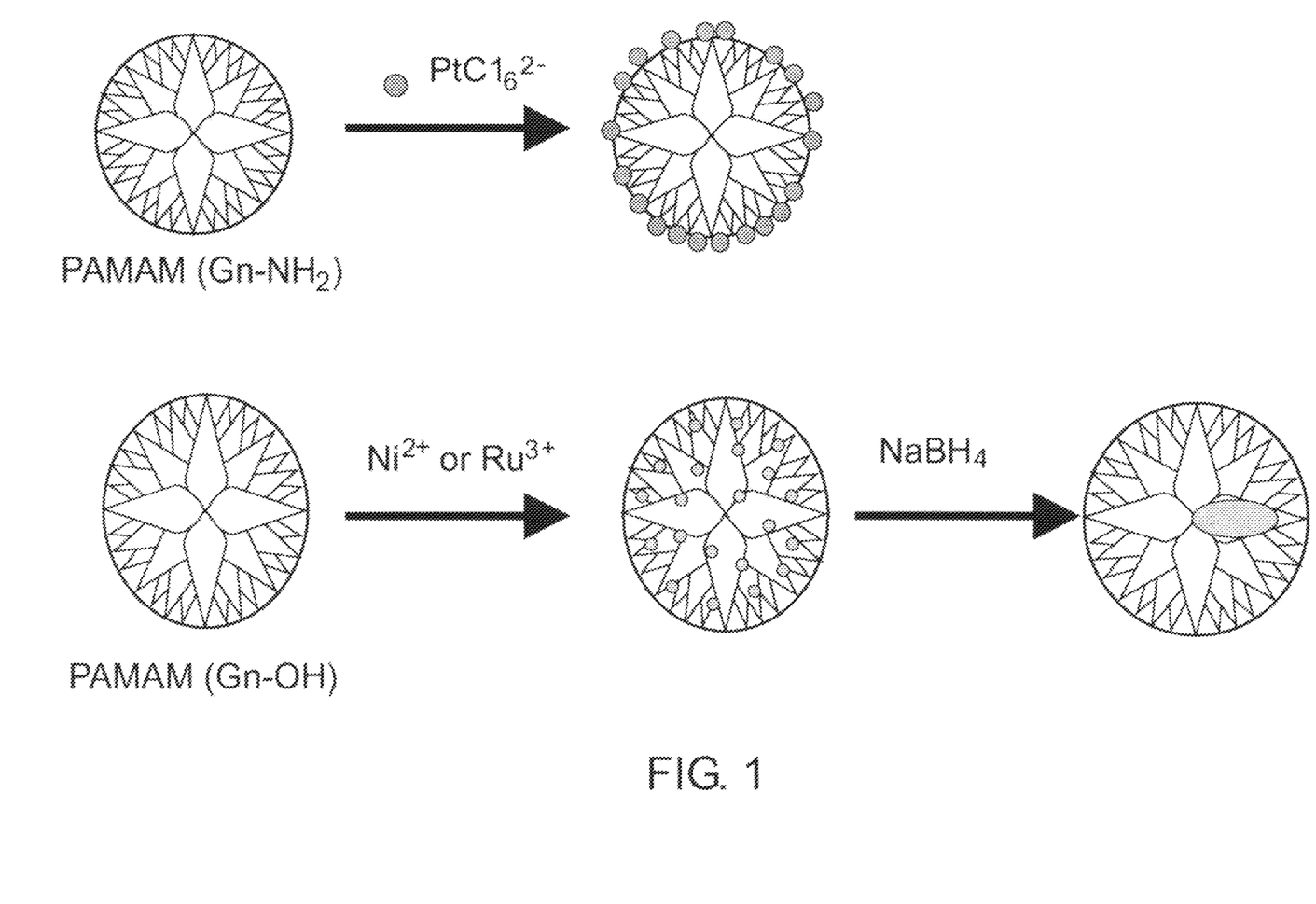
FIG. 1 is a schematic depicting nanoparticle synthesis derived from a dendrimer template.

To develop hollow nanoparticles for enhancing the figure of merit (ZT) of thermoelectric (TE) materials, amine terminal dendrimer molecules are used to fabricate a metallic, particularly transition metals such as Ag, Pt, Au, Pd, Ni, Fe, Co, Mn, etc., lining on a dendrimer. Dendrimers are used as templates for preparation of nano-sized aggregates of metals including as few as approximately 40 to 50 atoms. Amine groups of the dendrimer molecules display a capability to generate anchor sites for transition metal ion complexation. The dendrimers act as both nanoscale templates and void generators. Hollow nanoparticles thus prepared within a bulk matrix material exhibit the process of phonon scattering which reduces thermal conductivity. The thermal conductivity within a crystalline structure of a material is due to both phonon and energetic electron transmission. For this integrated structural embodiment and environmental conditions, the transfer of thermal energy by phonons is the dominant process as compared to energetic electrons. The hollow nanoparticles, or metallic nanoshells, prepared by dendrimer templates are the main structure for phonon scattering. In addition to lowering the thermal conductivity, the hollow metal nanoparticles are excellent electrical conductors, thus further enhancing the ZT. Dendrimer-templated nanoparticles are particularly successfully formed from transition metal ions such as Cu, Pd, Pt, and Au and a semiconductor, CdS. Dendrimer molecules used for creating nanoparticles preferably include amine-terminated poly(amidoamine) (PAMAM) dendrimers (G4(NH$_2$), where G4 represents the 4$^{th}$ generation) and hydroxyl-terminated PAMAM (G5(OH)) (see FIG. 1) (I modified figure and check all figures); other dendrimer molecules may be used as well.

In this work, discrete, well-defined polymers known as dendrimers are used as templates to control the size, stability, and solubility of nanoparticles ranging in metal lining thicknesses from less than 5 nm to several tens of nanometers. The diameter of the void is controlled by the dendrimer generation used in the process.

Figure 2:
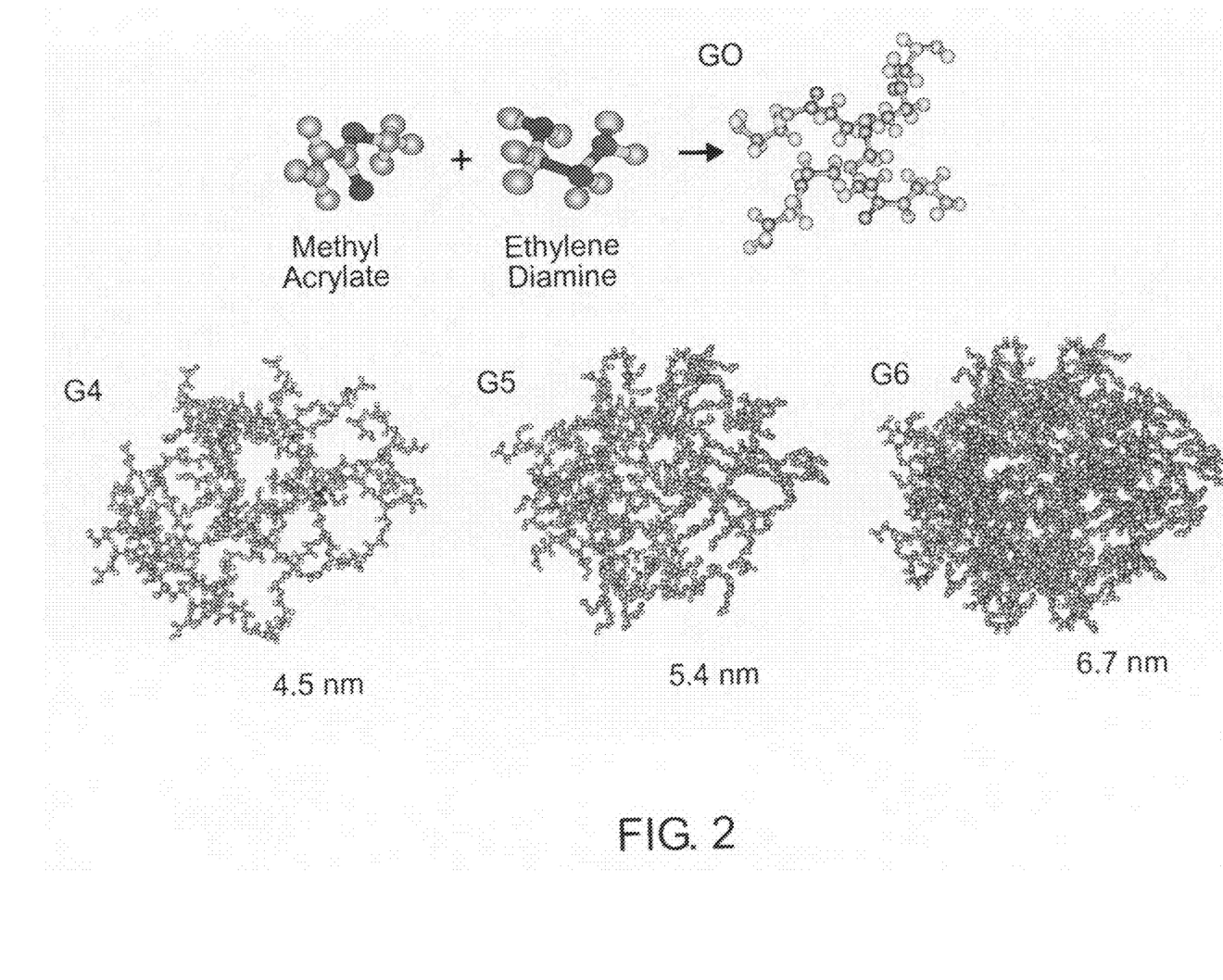
FIG. 2 is a drawing depicting the growth of poly(amidoamine) dendrimer[10]

The dendrimer template usually serves to both control particle size and passivate the surface of the nanoparticles against agglomeration. Many different types of metallic and semiconducting nanoparticles are prepared using various kinds of templates. Monolithic ceramic and polymeric templates are used for preparing nanomaterials. For example, the well-defined pores in alumina or polymeric filtration membranes can be used to define the geometric and chemical properties of metal, semiconductor, and polymeric nanomaterials. In many cases the template can be removed chemically or thermally, thus leaving behind the pristine nanomaterials. The obvious advantage of this technique is that highly monodisperse particles with a variety of shapes, sizes, and chemical compositions can be prepared. The chemical structure of the dendrimer PAMAM is shown in FIG. 2. The number of functional groups on the dendrimer surface increases exponentially as a function of generation and the resulting steric crowding on the periphery causes geometrical changes. For example, the Generation 1 (G1) PAMAM dendrimer shown in FIG. 2 has an expanded or "open" structure, the G4 has a porous, globular structure and the G6 has a spheroid structure with a somewhat impenetrable surface. Growth of the dendrimer proceeds by exponential addition of ammonia or ethylene diamine to a core molecule. A repeat unit, methyl acrylate, replaces the hydrogen atoms. A branch cell, ethylene diamine, is then added easily. Together, these monomers constitute the basic building blocks of the dendrimer. The unattached end of this unit has two nitrogen-hydrogen bonds; preferably the two steps are repeated to affix two more sections to the growing structure. The unattached end of the structure has four nitrogen-hydrogen bonds, allowing four units to be attached subsequently. The repetition process gives rise to the complicated final structure. The PAMAM used as templates in this work are a three-dimensional hyperbranched polymer.

The structural parameter of PAMAM dendrimers are represented in Table I. The fourth generation dendrimer with amine terminal groups has a theoretical diameter of 4.5 nm and 64 surface amine groups. The theoretical diameter of the sixth generation dendrimer is 6.7 nm.

TABLE I

Structural parameters of Starburst ® poly(amidoamine) dendrimer

| Generation | M. W. | Diameter (Å) | No. of Surface groups |
|---|---|---|---|
| 0 | 517 | 15 | 4 |
| 1 | 1,430 | 22 | 8 |
| 2 | 3,256 | 29 | 16 |
| 3 | 6,909 | 36 | 32 |
| 4 | 14,215 | 45 | 64 |
| 5 | 28,826 | 54 | 128 |
| 6 | 58,048 | 67 | 256 |
| 7 | 116,493 | 81 | 512 |
| 8 | 233,383 | 97 | 1024 |
| 9 | 467,162 | 114 | 2048 |
| 10 | 934,720 | 135 | 4096 |

The driving force for guest encapsulation within dendrimers can be based on covalent bond formation, electrostatic interactions, complexation reactions, steric confinement, various types of weaker forces (van der Waals, hydrogen bonding, etc.), and combinations thereof. Many examples of dendrimer-based host-guest chemistry have been reported. While Cu$^{2+}$ interacts with tertiary amine groups by complexation, PtCl$_4^{2-}$ undergoes a slow ligand-exchange reaction involving substitution of one chloride ion for one interior tertiary amine. BH$_4^-$ reduction of PtCl$_4^{2-}$-G4(NH$_2$), which exists as a cross-linked emulsion, results in immediate precipitation of large Pt particles. In contrast, Gn(OH)-encapsulated particles do not agglomerate for up to 150 days, and they are redissolved in a solvent after repeated solvation/drying cycles.

Figure 3:
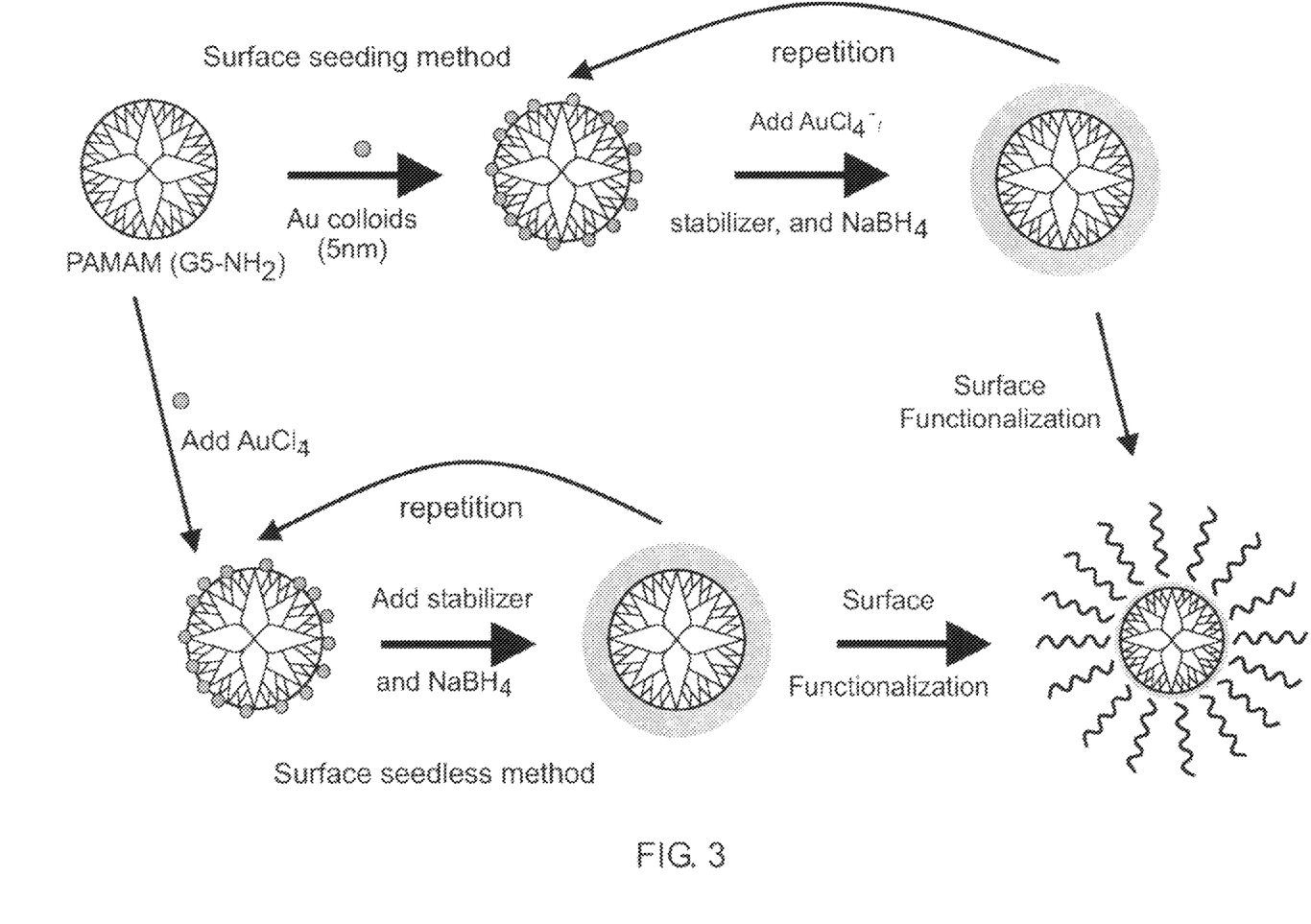
FIG. 3 is a schematic depicting fabrication of hollow nanoparticles using a dendrimer template.

FIG. 3 shows a schematic diagram of hollow nanoparticle fabrication using dendrimer templates. In this case we used a fifth generation amine terminal dendrimer as a template. In this particular fabrication, the unconjugated Au nanoparticles are necessary as a seeding material. Currently unconjugated Au nanoparticles are commercially available down to 2 nm size. Alternatively, Au nanoparticles can be formed simply in a laboratory. The first step is to attach Au colloids or Au ions to amine groups that exist on the dendrimer surface in stabilized solution through either the surface seeding method or the surface seedless method. The second step is to repeat the process with additional Au ions, stabilizer, and a reducing agent such as NaBH$_4$ to increase the wall thickness of Au lining on the dendrimer surface. Au ions are automatically reduced and settled on the Au nanoparticles, thus increasing its wall thickness. Acceptable stabilizers, such as boric acid, thiol terminated chemical molecules or a solvent, are commercially available. Through the repeated processes, the hollow Au nanoparticles are created, since the three dimensional structure of dendrimers has an interior with void spaces. The void size of hollow nanoparticles is dependent on the dendrimer generation. The thickness of Au thin film around the dendrimer is dependent on the number of repetition processes and the size of initial Au seeds. Also, we can functionalize the surface of Au nanoshells with various chemicals to enhance the miscibility with Si, Ge, Bi, Te and other precursors. For thermoelectric applications, the functionalized metal nanoshells are mixed with precursors of base TE materials to develop an embedded structure of the metal nanoshells into bulk TE materials.

Figure 4:
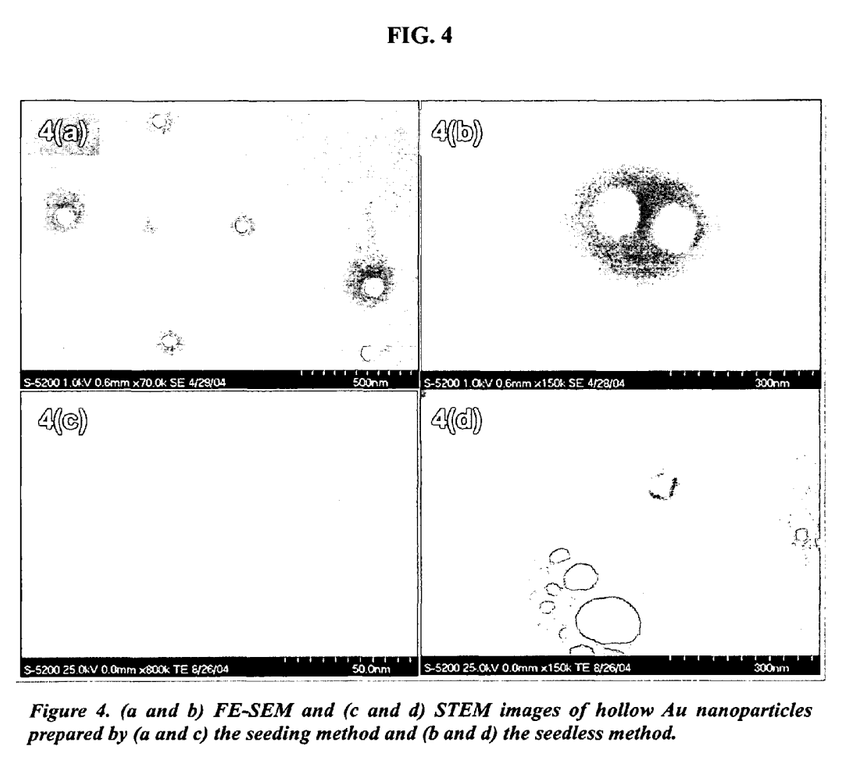
FIG. 4a is a drawing prepared from an FE-SEM image of hollow Au nanoparticles prepared by the seeding method.
FIG. 4b is a drawing prepared from an FE-SEM image of hollow Au nanoparticles prepared by the seedless method.
FIG. 4c is a drawing prepared from an STEM image of hollow Au nanoparticles prepared by the seeding method.
FIG. 4d is a drawing prepared from an STEM image of hollow Au nanoparticles prepared by the seedless method.

FIG. 4 shows the scanning transmission electron microscope (STEM) images of hollow Au nanoparticles that were fabricated using dendrimer templates according to the preferred embodiment of the present invention. The hollow Au nanoparticles are developed to be uniform and well separated from each other. The outer diameter of hollow Au nanoparticles is around 80 nm. The wall thickness of the Au lining is about 5 nm under the seeding method and 20 nm under the seedless method.

Figure 5:
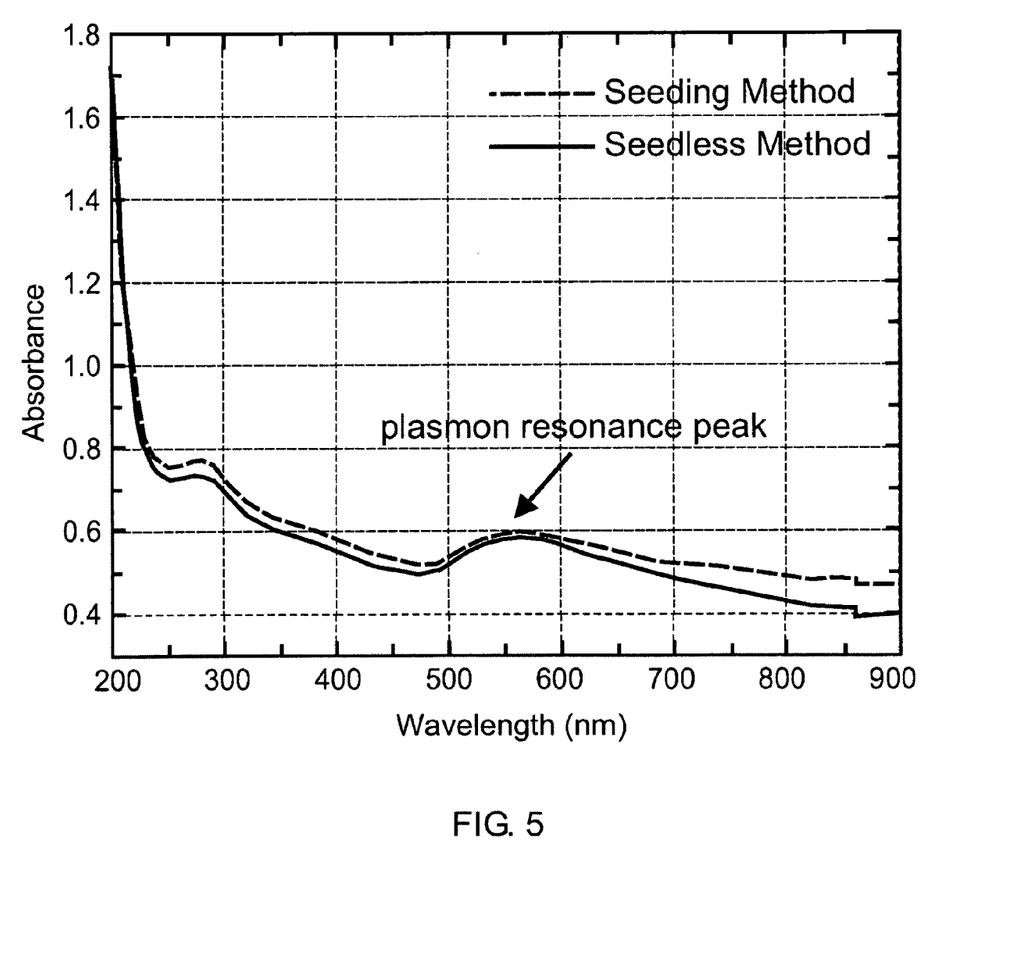
FIG. 5 is a graph depicting the UV-Visible absorption spectra of hollow Au nanoparticles prepared by the seeding method and the seedless method.

FIG. 5 shows the UV-visible absorption spectra of dendrimer-templated Au hollow nanoparticles prepared according to the present invention. Ultraviolet-visible (UV-Vis) spectra were obtained on a Perkin-Elmer Lambda 900 spectrometer. Spectra were measured from 900 nm to 200 nm at a scan speed of 150 nm/min. The presence of an absorption peak is attributed to the Mie plasmon resonance and indicates that the Au nanoparticles are larger than the Mie-onset particle diameter of about 5 nm. The band broadening and blue shifts of the plasmon resonance peak are as a function of the decrease of Au particle size. If the particle diameter exceeds about 20 nm, the resonance begins to broaden and shifts toward the red region due to radiation damping. The plasmon resonance cannot be detected for very small metal clusters because the peak is flattened due to the large imaginary dielectric constant for small metal particles and the wavelength dependent diffraction limit. Au nanoparticles with a size of 5 nm show a 520 nm resonance in water. This peak shifts only 25 nm to larger wavelength with an increase in size to 80 nm. Colloidal metal nanoshells can have resonances that can be tuned over a wide range as a function of the core-to-shell ratio. Metal hollow nanoparticles showed interesting surface plasmonic properties different from their solid counterparts. When dendrimer-templated hollow Au nanoparticles were made according to the present invention, a plasmon resonance peak appeared at about 550 nm. Normally, this peak shifted to a shorter wavelength as the size of the particle decreased and eventually disappeared. The broadness of the plasmon peak is likely due to the various sizes of the nanoparticles.

The surface of metallic nanoshells formed according to this method can be functionalized with various chemicals to enhance the mixibility with Si, Ge, Bi, and Te precursors. The functionalized metal nanoshells are mixed with precursors of base TE materials to embed the metal nanoshells to TE films.

Obviously, many modifications may be made without departing from the basic spirit of the present invention. Accordingly, it will be appreciated by those skilled in the art that within the scope of the appended claims, the inventions may be practiced other than has been specifically described herein. Many improvements, modifications, and additions will be apparent to the skilled artisan without departing from the spirit and scope of the present invention as described herein and defined in the following claims.

We claim:

1. A process for the fabrication of hollow metallic nanoshells, which process comprises:
    (a) providing at least one amine terminal dendrimer molecule;
    (b) promoting growth of the at least one amine terminal dendrimer molecule to form a dendrimer structure, having at least one surface amine group, for use as a template for the hollow metallic nanoshells;
    (c) attaching at least one metallic ion to the at least one surface amine group;
    (d) further attaching at least one metallic ion to the at least one surface amine group by adding additional metallic ions, boric acid, and a reducing agent, such that a wall forming at least one hollow metallic nanoshell is formed; and
    (e) removing the dendrimer structure from the hollow metallic nanoshells.

2. The process of claim 1, wherein the at least one amine terminal dendrimer molecule is an amine-terminated poly (amidoamine) (PAMAM) dendrimer.

3. The process of claim 2, wherein the at least one amine terminal dendrimer molecule is selected from the group consisting of PAMAM G4($NH_2$), G5($NH_2$), G6($NH_2$), G7($NH_2$), G8($NH_2$), and higher PAMAM generations, where G4 represents the $4^{th}$ generation of the PAMAM dendrimer, G5 represents the $5^{th}$ generation of the PAMAM dendrimer, G6 represents the $6^{th}$ generation of the PAMAM dendrimer, G7 represents the $7^{th}$ generation of the PAMAM dendrimer, and G8 represents the $8^{th}$ generation of the PAMAM dendrimer.

4. The process of claim 1, wherein the growth of the at least one amine terminal dendrimer molecule in (b) proceeds by exponential addition of a material selected from the group consisting of ammonia and ethylene diamine.

5. The process of claim 1, wherein the dendrimer structure formed in (b) is a three-dimensional hyperbranched polymer.

6. The process of claim 1, wherein the metallic ion of (c) and (d) is a transition metal.

7. The process of claim 1, wherein the metallic ion of (c) and (d) is selected from the group consisting of gold, copper, silver, palladium, nickel, iron, cobalt, manganese and platinum.

8. The process of claim 1, wherein the reducing agent is $NaBH_4$.

9. The process of claim 1, wherein the dendrimer structure is chemically or thermally removed from the hollow metallic nanoshells in (e).

10. A process for the fabrication of hollow semiconductor nanoshells, which process comprises:
    (a) providing at least one amine terminal dendrimer molecule;
    (b) promoting growth of the at least one amine terminal dendrimer molecule to form a dendrimer structure, having at least one surface amine group, for use as a template for the hollow semiconductor nanoshells;
    (c) attaching at least one semiconductor to the at least one surface amine group;
    (d) further attaching at least one semiconductor to the at least one surface amine group by adding additional semiconductor, a stabilizer, and a reducing agent, such that a wall forming at least one hollow semiconductor nanoshell is formed; and (e) removing the dendrimer structure from the hollow semiconductor nanoshells.

11. The process of claim 10, wherein the at least one amine terminal dendrimer molecule is an amine-terminated poly(amidoamine) (PAMAM) dendrimer.

12. The process of claim 11, wherein the at least one amine terminal dendrimer molecule is selected from the group consisting of PAMAM $G4(NH_2)$, $G5(NH_2)$, $G6(NH_2)$, $G7(NH_2)$, $G8(NH_2)$, and higher PAMAM generations, where G4 represents the $4^{th}$ generation of the PAMAM dendrimer, G5 represents the $5^{th}$ generation of the PAMAM dendrimer, G6 represents the $6^{th}$ generation of the PAMAM dendrimer, G7 represents the $7^{th}$ generation of the PAMAM dendrimer, and G8 represents the $8^{th}$ generation of the PAMAM dendrimer.

13. The process of claim 10, wherein the growth of the at least one amine terminal dendrimer molecule in (b) proceeds by exponential addition of a material selected from the group consisting of ammonia and ethylene diamine.

14. The process of claim 10, wherein the dendrimer structure formed in (b) is a three-dimensional hyperbranched polymer.

15. The process of claim 10, wherein the semiconductor of (c) and (d) is cadmium sulfide.

16. The process of claim 10, wherein the reducing agent is $NaBH_4$.

17. The process of claim 10, wherein the stabilizer is selected from the group consisting of boric acid, thiol terminated chemical molecules and a solvent.

18. The process of claim 10, wherein the dendrimer structure is chemically or thermally removed from the hollow semiconductor nanoshells in (e).

* * * * *